March 2, 1976 R. H. McCOLLEY Plant Pat. 3,831
PHILODENDRON PLANT
Filed Nov. 1, 1974
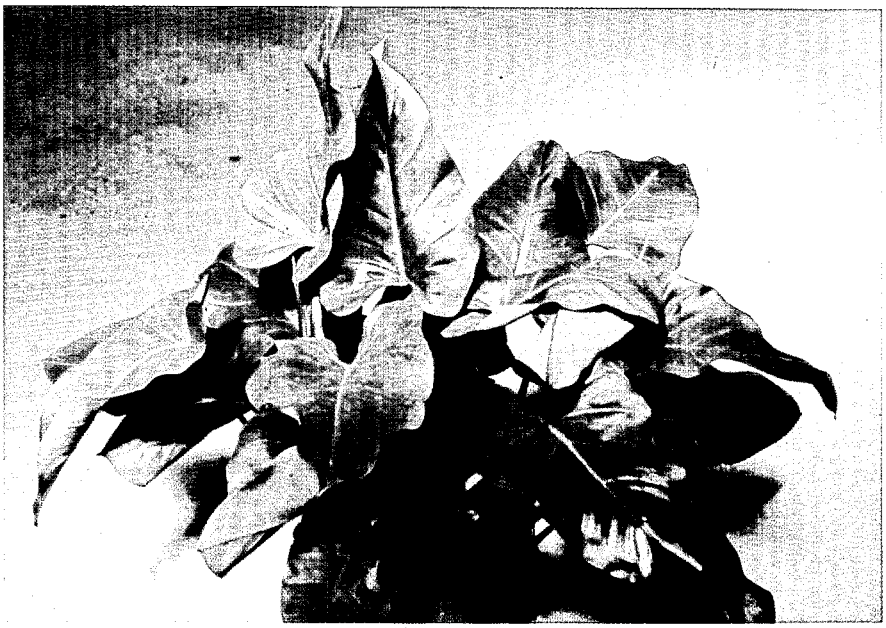

United States Patent

Plant Pat. 3,831
Patented Mar. 2, 1976

3,831
PHILODENDRON PLANT

Robert H. McColley, P.O. Box 17126,
Orlando, Fla. 32810

Filed Nov. 1, 1974, Ser. No. 520,106
Int. Cl. A01h *5/00*
U.S. Cl. Plt.—88 1 Claim

ABSTRACT OF THE DISCLOSURE

The disclosure herein is a philodendron plant, characterized by its resistance to wilting under low moisture and high temperature conditions, its slow growth and retention of form indoors, thick, rubbery, generally ovate shaped leaves which are a strong yellow on new leaves, with the bottom leaves being dark, yellowish green.

DESCRIPTION OF THE INVENTION

I identify my present invention as Royal King, the same comprising a new and distinct variety of Philodendron plant which I have developed by pollinating the standard plant in my greenhouse with pollen from a seedling selected by me from the same seedling and self breeding. The standard plant which provides a basis, is from a seedling selected by me for a breeding program which I have carried on for many years involving several Philodendron species specifically *imbe, wendlandi, erubescens* and *hastatum.*

The color of the plants of my invention is new to Philodendrons and is further distinguished by its excellent keeping qualities under low humidity and high temperature conditions.

My new variety has been asexually reproduced by single eye cuttings as well as tip cuttings in the vicinity of Orlando, Fla., and has been found to retain its distinctive characteristics through successive asexual reproduction.

Testing of my new variety has been undertaken in California and Florida under adverse conditions, and has proven itself to be a superior foliage plant in each case.

I know of no similarity of the instant plant to any Philodendron in cultivation, nor to any described by Graf, Bailey or Das Pflansenreich.

Present visual characteristics of my new variety make the same distinctive and recognizable, including the ovate leaf shape, the base of the mature leaf being cordate and the immature or juvenile leaf also being cordate.

The tips of the leaves are acute and the venation pinnate. The leaves have smooth midribs, sunken veins, and the surfaces are smooth to undulate.

The width of the leaves on the average is about 65% of the length. The plant form appears dense; the petioles being erect and of medium length.

During growth, the leaves assume horizontal to semi-pendant positions and the internodes are close.

Certain general characteristics of my new variety, include the ability to withstand extremely low light intensity and low soil moisture content for weeks.

High temperatures do not seem to bother the plant seriously.

The leaves of the plant are medium thick, rubbery, and withstand bruising and dehydration.

The plant is virtually immune to "shot gun" fungus, and resistant to bacterial soft rot.

Indoor growth of the plant is slow, the desired form being retained as long as varieties currently available.

The following detailed specifications are based on observations made in my greenhouse in Orlando, Fla. These specifications may be affected somewhat by varying environmental conditions, but where environmental conditions remain such as those present during development, including temperature, humidity and day length, the plants will reproduce and develop uniformly.

The accompanying drawing, forming a part of the specification, shows a typical plant of my new variety, the colors being as nearly true as possible with color illustrations of this type. Color references are made to the Nickerson Color Fan published by Munsell Color Company with observations being recorded by daylight illumination under vinyl of not more than 30% shade.

I. Form characteristics

1. Leaf shape:
   (*a*) *Mature.*—Ovate.
   (*b*) *Immature.*—Ovate.
   (*c*) *Tip.*—Acute.
   (*d*) *Base.*—(1) Mature Cordate. (2)—Immature Cordate.
   (*e*) *Displacement.*—Smooth.
   (*f*) *Margin.*—Entire.
   (*g*) *Venation.*—Slightly sunken.
2. Leaf attachment Stalked.
3. Leaf arrangement: Alternate, horizontal, slightly pendant.
4. Petiole; Short length, slightly winged, horizontal to slightly erect.
5. Stem: Short, heavy internodes ½" to ¾".
6. Overall appearance: Dense.

II. Size characteristics of typical commercial size

1. Leaf itself:
   (a) *Width (widest point).*—5¼".
   (*b*) *Width (1" from tip).*—2".
   (*c*) *Length.*—8".
2. Petiole:
   (*a*) *Length.*—5½".
   (*b*) *Diameter (center).*—¼"–⅜".
   (*c*) *Internode spacing.*—¾".
   (*d*) *Stem diameter.*—½"–¾".

III. Color characteristics

1. Leaf:
   (*a*) *Top (new leaves).*—5Y 7/10.
   (*b*) *Bottom overlay.*—2.5R 7/8.
   (*c*) *Margin.*—2.5R 4/10.
2. Leaf (old bottom leaves):
   (*a*) *Top darker.*—10GY 4/5.
   (*b*) *Bottom lighter.*—5GY 5/6.
   (*c*) *Margin.*—2.5R 4/10.
3. Leaf venation (underside):
   (*a*) *Midrib.*—2.5R 3/7.
   (*b*) *Veins.*—2.5R 3/7.
4. Stem: 5R 3/7.
5. Petiole: 2.5R 3/7.

I claim:

1. A new and distinct variety of Philodendron plant, substantially as herein disclosed, characterized as to novelty by its ability to withstand low moisture and high temperature conditions, its slow growth and retention of form indoors, its rubbery, generally ovate shaped leaves which are yellow-green and have dark red petioles and stems.

No references cited.

ROBERT E. BAGWILL, Primary Examiner